(12) United States Patent
Weiss et al.

(10) Patent No.: US 8,339,256 B2
(45) Date of Patent: Dec. 25, 2012

(54) RADIOFREQUENCY SAFETY OF SWITCHABLE SEGMENTED TRANSMISSION LINES

(75) Inventors: Steffen Weiss, Hamburg (DE); Oliver Lips, Hamburg (DE); Sascha Krueger, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 553 days.

(21) Appl. No.: 12/645,549

(22) Filed: Dec. 23, 2009

(65) Prior Publication Data

US 2010/0134273 A1    Jun. 3, 2010

Related U.S. Application Data

(63) Continuation-in-part of application No. 12/375,750, filed as application No. PCT/IB2007/052832 on Jul. 16, 2007, now Pat. No. 7,999,549.

(30) Foreign Application Priority Data

Aug. 2, 2006  (EP) .................................. 06118280

(51) Int. Cl.
G08B 1/00     (2006.01)
A61B 5/05     (2006.01)

(52) U.S. Cl. ......... 340/532; 340/531; 340/537; 600/423

(58) Field of Classification Search ............... 340/531, 340/532, 536, 537, 573.1; 324/318, 322, 324/637; 156/345.37, 345.48; 600/411, 600/421, 423
See application file for complete search history.

(56) References Cited

U.S. PATENT DOCUMENTS

| | | | | |
|---|---|---|---|---|
| 5,121,067 A | * | 6/1992 | Marsland | 324/637 |
| 5,681,418 A | * | 10/1997 | Ishimaru | 156/345.37 |
| 6,496,714 B1 | * | 12/2002 | Weiss et al. | 600/423 |
| 6,710,597 B2 | * | 3/2004 | Reykowski et al. | 324/318 |
| 7,082,325 B2 | * | 7/2006 | Hashimshony et al. | 600/411 |

* cited by examiner

Primary Examiner — Van T. Trieu

(57) ABSTRACT

A magnetic resonance imaging (MRI) system includes an interventional instrument and a switched, segmented transmission ($T_x$) line which ensures safety during an MRI protocol while the interventional instrument is located in the system. The transmission line includes at least two electrically conductive $T_x$ line segments separated by a non-conductive gap. An electrically conductive bridge, having an open and a closed state, and a parallel connected impedance bridge, having a known impedance which suppresses RF current between the line segments, bridge the non-conductive gap. A measurement unit measures the impedance across the $T_x$ line while the conductive bridges are open. The line segments are verified to be decoupled if the measured impedance of the line is substantially equal to that of the impedance bridge.

19 Claims, 4 Drawing Sheets

RADIOFREQUENCY SAFETY OF SWITCHABLE SEGMENTED TRANSMISSION LINES

CROSS-REFERENCE TO RELATED APPLICATION

The present application is a continuation-in-part of International (PCT) Patent Application Publication No. WO 2008/015605, (PCT/IB2007/052832) filed Jul. 16, 2007, which claims the benefit of priority to EP 06118280.4, filed Aug. 2, 2006.

BACKGROUND AND SUMMARY

The present application relates to a transmission cable for use in radio frequency (RF) electrical and/or magnetic fields. It finds particular application in conjunction with magnetic resonance imaging (MRI) system and will be described with particular reference to galvanic isolation when guided through radio frequency (RF) electrical and/or magnetic fields of an MR imaging system.

A MR imaging system is often used for the examination and treatment of patients. By such a system, the nuclear spins of the body tissue to be examined are aligned by a static main magnetic field $B_0$ and are excited by transverse magnetic fields $B_1$ oscillating in the radiofrequency band. The resulting relaxation signals are exposed to gradient magnetic fields to localize the resultant resonance. The relaxation signals are received in order to form in a known manner a single or multiple dimension image.

Use is made of active interventional devices which are introduced into the patient, for example, it is highly desired to perform interventional procedures under MRI guidance in order to improve therapy outcome and to reduce radiation exposure. Transmission lines or paths are provided for connecting the distal tip and/or other components of the interventional device, such as catheters, needles, stents, imaging coils, guidewires, and the like, with an active unit, notably a power supply, a receiving/transmission device, a control unit, or the like. The active interventional devices usually have to be guided through MR fields which in the case of an MR system includes the $B_1$ field, generated in the form of RF pulses which are transmitted by the RF coil system. Such RF fields may induce common mode signals (currents) in the transmission line and in the surrounding body tissue. Such common mode signal can cause large electric fields. These currents create not only the risk of disturbances or destruction of the accessory device and/or the active unit, but notably they can give rise to substantial heating of the adjacent tissue resulting in potentially severe burns of inner organs or blood/tissue coagulation for the patient.

For example, it is highly desired to perform electrophysiology (EP) interventions under MRI guidance in order to improve therapy outcome and to reduce X-ray exposure. One method to realize RF safe active interventional devices is to segment the transmission line into short, non-resonant segments, which are mechanically connected during the intervention or mechanically disconnected during imaging. However, there is no mean to verify that the line segments are decoupled from one another to ensure safety from RF induced common mode currents, short circuits, or the like.

The present application provides a new and improved system and method which overcomes the above-referenced problems and others.

In accordance with one aspect, a transmission line for use in a radio-frequency and/or magnetic field is presented. The transmission line includes at least two electrically conductive transmission line segments separated by a non-conductive gap. The gap is bridged by an electrically conductive bridge which has two states: a closed state which electrically connects two of the transmission line segments across the non-conductive gap and a open state which electrically disconnects the at least two transmission line segments across the non-conductive gap. An impedance bridge is connected electrically in parallel to the electrically conductive bridge to bridge the non-conductive gaps, each impedance bridge has an impedance which is chosen to suppress radiofrequency (RF) induced current between the line segments. A bridge controller is operatively connected to the conductive bridge to control its one of two states. A measurement unit measures the impedance across the line segments and the impedance bridge while the conductive bridge controlled to be in the open state.

In accordance with another aspect, a method of using a transmission line is presented. The transmission line includes at least a pair of transmission line segments separated by a non-conductive gap. The non-conductive gap is bridged by a conductive bridge which is parallel to an impedance bridge. The method comprises of installing the transmission line in an interventional instrument, such as a catheter. The conductive bridge is controlled to an open state such that the line segments are electrically decoupled. An impedance of the impedance bridge is measured.

One advantage resides in that safety for a patient and equipment is improved.

Still further advantages of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
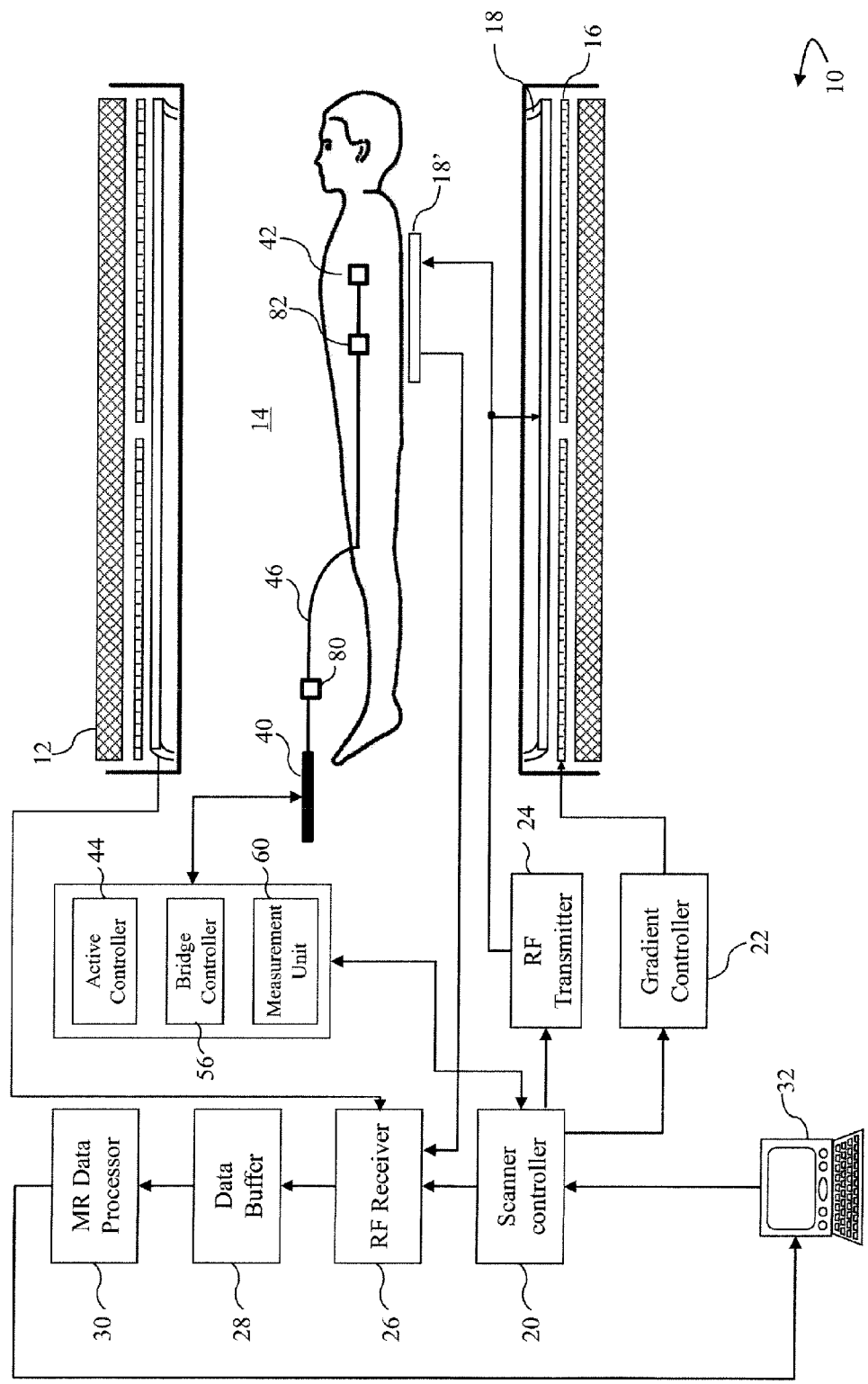
FIG. 1 is a diagrammatic illustration of an magnetic resonance imaging system along with an interventional instrument with a switchable, segmented transmission line.

With reference to FIG. 1, a magnetic resonance imaging system 10 includes a main magnet 12 which generates a temporally uniform $B_0$ field through an examination region 14. The main magnet can be an annular or bore-type magnet, a C-shaped open magnet, other designs of open magnets, or the like. Gradient magnetic field coils 16 disposed adjacent the main magnet serve to generate magnetic field gradients along selected axes relative to the $B_0$ magnetic field. A radio frequency coil, such as a whole-body radio frequency coil 18 is disposed adjacent the examination region. Optionally, local or surface RF coils 18' are provided in addition to or instead of the whole-body RF coil 18.

A scan controller 20 controls a gradient controller 22 which causes the gradient coils to apply selected magnetic field gradient pulses across the imaging region, as may be appropriate to a selected magnetic resonance imaging or spectroscopy sequence. The scan controller 20 also controls an RF transmitter 24 which causes the whole-body or local RF coils to generate magnetic resonance excitation and manipulation $B_1$ pulses. The scan controller also controls an RF receiver 26 which is connected to the whole-body or local RF coils to receive magnetic resonance signals therefrom.

The received data from the receiver 26 is temporarily stored in a data buffer 28 and processed by a magnetic resonance data processor 30. The magnetic resonance data processor can perform various functions as are known in the art, including image reconstruction, magnetic resonance spectroscopy, catheter or interventional instrument localization, and the like. Reconstructed magnetic resonance images, spectroscopy readouts, interventional instrument location information, and other processed MR data are displayed on a graphic user interface 32. The graphic user interface 32 also includes a user input device which a clinician can use for controlling the scan controller 20 to select scanning sequences and protocols, and the like.

An interventional instrument 40, such as a catheter, is held by the surgeon or clinician. Various other types of interventional instruments and catheters are contemplated. For example, the catheter may include a guide wire, a stent, an injector, a passage for introducing contrast agents or other fluids, etc. The interventional instrument has an active element 42 disposed at a tip end thereof. Various electrical functions can also be performed in the interventional instrument with the active element. In one embodiment, the active element is an electrophysiology (EP) probe for diagnosis and treatment of cardiac arrhythmia. The probe may be used for mapping in order to locate aberrant electrical pathways and currents within the heart, as well as for diagnosing mechanical and other aspects of cardiac activity. Alternatively, the probe may be used for treatment by ablating and killing cardiac tissue in order to create non-conducting lesions that disrupt the abnormal electrical pathway causing the arrhythmia. It should be understood that the illustrated embodiment has been set forth only for the purposes of example and that other interventional devices are also contemplated, such as devices with an electrical element disposed along the length of or in the tip of the intervention device. e.g. pacemaker, nuerostimulator, defibrillator, or the like. Furthermore, the term "active" refers to an active device 42 which is electrically connected to electrical equipment for transmission or detection of electrical signals. The active element 42 can be an active device which is externally powered, such as any number of sensors, or a passive device, such as electrodes used for EP mapping. Optionally, other electrical equipment such as an amplifier, matching and tuning circuitry, or other circuitry, may be disposed in the tip of the catheter adjacent the active element, e.g. the EP probe.

The active element 42 is electrically connected to an active element controller 44 via a switched, segmented transmission line (SSTL) 46. The SSTL is able to transmit any type of signal that may be required for the respective functionality of the active element 42 and can be also used to deliver power to active parts of the instrument. In the example of the EP probe, the active element controller 44 is a power source and/or RF signal generator and antenna for mapping and treating target volumes.

Figure 2:
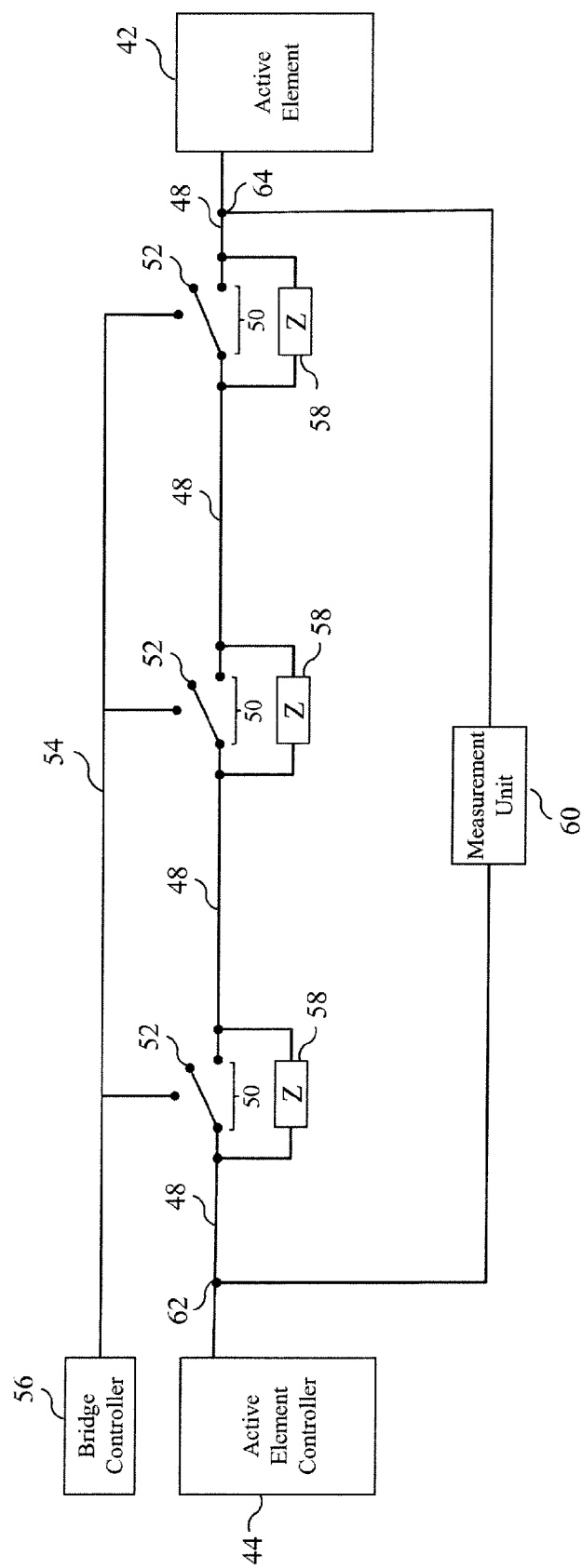
FIG. 2 is a diagrammatic illustration of the switchable, segmented transmission line with impedance bridges.

With reference to FIG. 2, the SSTL 46 includes segments of transmission ($T_x$) line 48 that are separated from one another by a non-conductive gaps 50. The $T_x$ line segments 48 are coupled to one another by electrically conductive bridges 52, e.g. switches or the like. Each bridge 52 has two states, an open state where two separated $T_x$ line segments are electrically disconnected across a gap 50 and a closed state where two separated $T_x$ line segments are electrically connected across a gap 50. The bridges 50 are spaced at not more than quarter wavelength intervals of the magnetic resonance excitation and manipulation $B_1$ pulse frequency in order to suppress the transfer of direct currents, off-resonance frequency currents, and common-mode resonance between the active element controller 44 and the active element 42.

Each bridge is actuated, i.e. from the open state to the close state or vice versa, by a non-electrical control line 54. An electrical control would be susceptible to currents induced by an electrical and/or magnetic field which, as previously mentioned, poses a risk to the subject, clinician user, and the equipment. The control line 54 is operatively connected to a bridge controller 56 which controls the mechanical, hydraulic, or pneumatic actuating systems or the like. The bridge controller 56 receives a signal from the scanner controller 20 to set the open/closed state of the conductive bridges 52. For example, prior to commencing an MR imaging protocol, particularly the MR excitation portion of the protocol, the $T_x$ line segments 48 are decoupled or after an MR imaging protocol or the excitation portion has terminated, the line segments 48 are coupled in order to operate the interventional instrument 40, active element 42, and/or send data from the active element.

In one embodiment, the control line 54 actuates the bridges 52 by a mechanical control line which applies a mechanical force on a bridge 52 to bring the two adjacent $T_x$ line segments 48 in electrical contact with each other. For example, non-conductive elements push and/or pull the bridges 52 to open or close the non-conductive gaps 50. Optionally, a non-conductive rod arranged substantially parallel to the transmission line 46 carries spring mounted contacts which when aligned adjacent to the non-conductive gaps 50 bridges the non-conductive gaps. The non-conductive rod may be translated, rotated out of alignment, or the like. In a further example, the $T_x$ line segments 48 are separated by an elastic member such as a spring, rubber gasket, or the like which exerts an outward force to separate and maintain the non-conductive gap 50 between the line segments 48. When an inward force is applied to the line segments 48, the elastic member compresses to bridge the non-conductive gap. Other mechanical means for actuating the bridges 52 not described are also contemplated.

In another embodiment, the control line 54 actuates the bridges 52 by a hydraulic control line which applies a hydraulic force on each bridge 52 to bring two adjacent $T_x$ line segments 48 in electrical contact with each other. The control line is filled with a suitable non-conductive fluid which when pressurized exerts a force on a conductive diaphragm, piston, or the like aligned with each bridge 52. The conductive diaphragm extends into the non-conductive gaps 50 to bridge adjacent line segments 48. Optionally, the diaphragm is non-conductive and applies a force to a conductive element which bridges the non-conductive gap 50. Alternatively, the diaphragms are actuated pneumatically. Other hydraulic or pneumatic means for actuating the bridges 52 not described are also contemplated. The hydraulic or pneumatic control line is hermetically sealed in order to mitigate harm to a subject.

Safety is compromised if one or more of the conductive bridges 52 remains closed during an imaging protocol. To ensure the state of the conductive bridges, impedance bridges 58 are disposed across the non-conductive gaps 50 and parallel to the conductive bridges 52. The impedance Z of the impedance bridges 58 are chosen to be sufficiently high enough to suppress inducted common mode currents. However, the Z values of the impedance bridges 58 are also chosen to be easily and reliably measured, e.g. Z=50 kΩ. In essence, when n conductive bridges are in an open state, the impedance across the transmission line 46 is not infinity; instead, the impedance is n*Z, where n is the number of impedance bridges and Z is the impedance of an individual bridge. When the conductive bridges 52 are in closed states, electrical currents along the transmission line 46 will travel through the conductive bridges 52, thus the impedance bridges 58 do not affect the performance of the active element 42. A measurement unit 60 measures the impedance across the $T_x$ line 46 at ports 62 and 64.

Since the conductive portions 48 of the transmission line 46 have little effect on the overall impedance, a measured impedance that is the proper multiple of Z indicates that all of the bridges 52 are in an open state. The scanner controller 20 receives a signal from the measurement unit 60 characteristic of the open/closed state of the conductive bridges 52. For example, prior to commencing an MR imaging protocol the measurement unit 60 measures the impedance across the $T_x$ line 46 to determine the status of the conductive bridges. Until a measured impedance is the known multiple of Z, i.e. all of the bridges 52 are decoupled, the imaging protocol is blocked from commencing.

Figure 3:
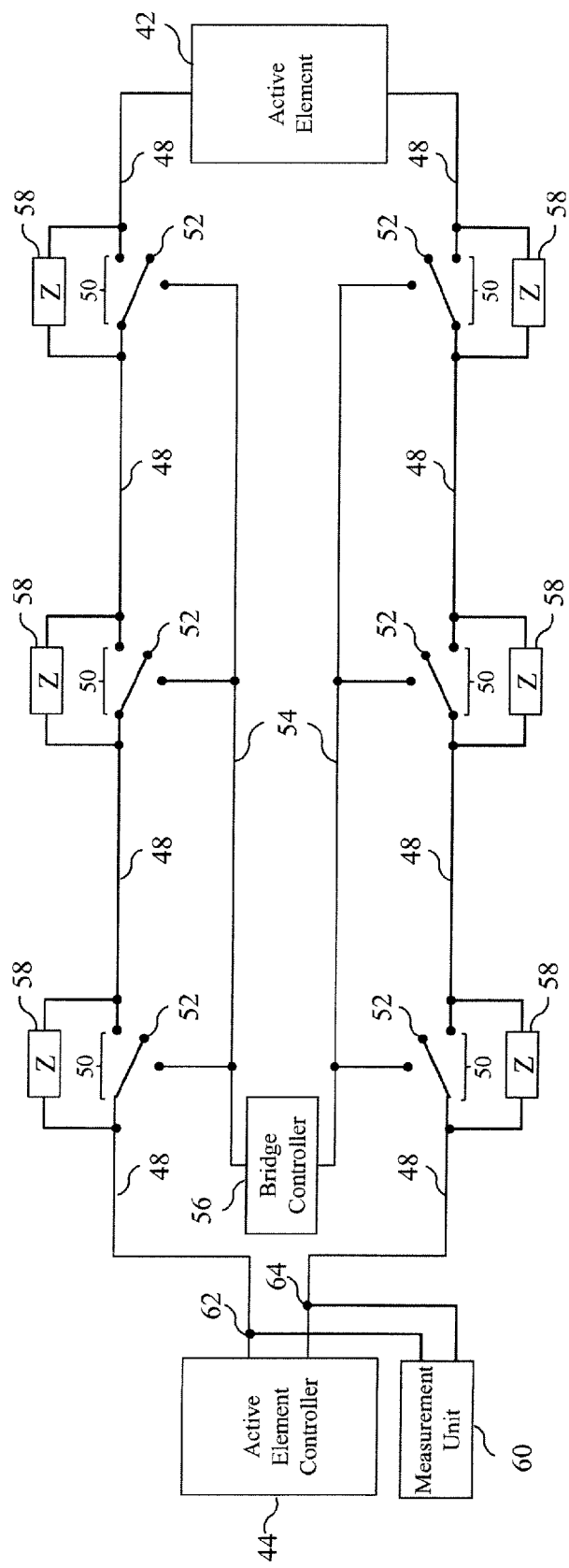
FIG. 3 is a diagrammatic illustration of a two conductor switchable, segmented transmission line with impedance bridges.

With reference to FIG. 3, in another embodiment, if the transmission line 46 uses two or more conductors, then the other conductors(s) include the conductive bridges, impedance bridges, non-conductive gaps, and the controls described above. The measurement unit 60 measures the impedance across a pair conductors or one conductor and ground at ports 62 and 64. Alternatively, the patient can serve as the ground connection.

Figure 4A:
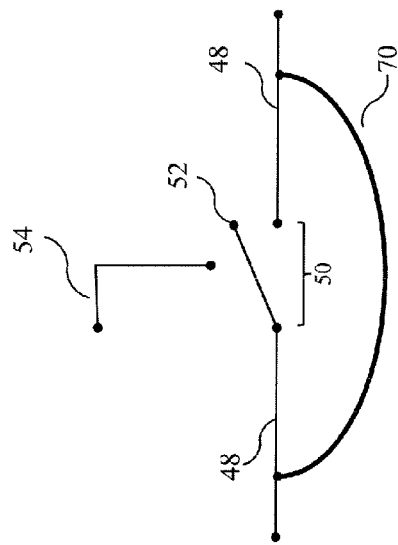
FIGS. 4A-4C are diagrammatic illustrations of various embodiments of the switchable, segmented transmission line with impedance bridges.

In one embodiment, the impedance bridge 58 includes a lumped impedance network composed of any combination of resistors, inductors, and capacitors, where a resistive network being the simplest and most economical. A lumped resistive network can be bulky and is susceptible to heating since the power is deposited highly localized. With reference to FIG. 4A, alternatively, a highly resistive lead wire 70 is disposed parallel to the conductive bridges 52 which can produce the reliable and easily measured resistivity to suppress common mode signals. The resistive lead wire 70 also distributes heating over its entire length, and thus less prone to overheating. Furthermore, the lead wire 70 can be thin keeping space requirements low.

Figure 4C:
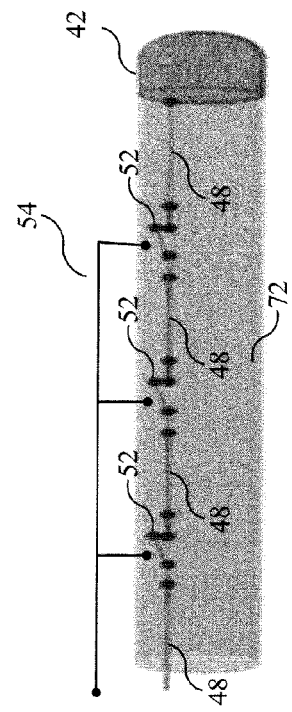
Figure 4B:
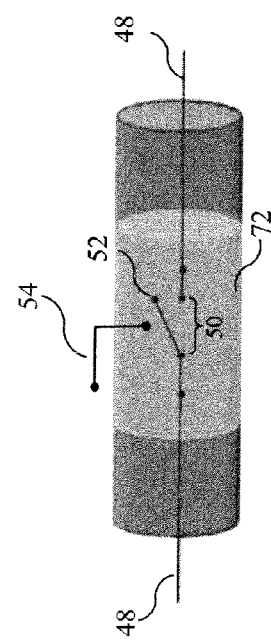

With reference to FIG. 4B, in another embodiment, the impedance bridge is realized by a conductive fluid 72 locally surrounding the conductive bridges 52. Ionic solutions of physiological concentration are used for cooling purposes in interventional procedures, such as ablation or the like, typically have a conductivity of 0.5 s/m. For a 0.5 mm tube at a 5 mm length, the resulting resistance is Z=50kΩ which is sufficient to block induced common mode currents. The dimensions and ionic concentration and thus the resulting resistance can be adjusted according to the interventional procedure. Alternatively, the conductive fluid 72 populates the entire interventional instrument as illustrated in FIG. 4C or circulated through a cooling line which may also serve as cooling an active element, e.g. an ablation probe. The fluid can optionally function as a hydraulic portion that powers the control system 56.

In one embodiment, the interventional instrument 40 includes a field sensor 80, such as a reed switch, RF antenna, or the like, for detecting RF electrical and/or magnetic fields. The field sensor status is communicated to the switching controller. In presence of a field, the switching controller decouples transmission line segments in the presence of a field by setting the electrically conductive bridges to an open state. The measuring unit measures the impedance along the transmission line to ensure the electrically conductive bridges are open.

In one embodiment, the interventional instrument 40 includes a temperature sensor 82 for detecting a temperature proximate to a treatment volume of the active element (e.g. ablation therapy) or along the transmission line. A value representative of the detected temperature is communicated to the switching controller for evaluation. If the detected temperature exceeds a predetermined value, the switching controller decouples the transmission line segments by setting the electrically conductive bridges to an open state. The measuring unit measures the impedance along the transmission line to ensure the electrically conductive bridges are open.

In another embodiment, the active element includes an RF transceiver coil.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A transmission line for use in a radio-frequency and/or magnetic field, comprising:
    at least two electrically conductive transmission line segments separated by a non-conductive gap;
    an electrically conductive bridge having two states, a closed state which electrically connects two of the transmission line segments across the non-conductive gap and a open state which electrically disconnects the at least two transmission line segments across the non-conductive gap;
    an impedance bridge connected electrically in parallel to the electrically conductive bridge which electrically connects the line segments across the non-conductive gaps, the impedance bridge having an impedance which suppresses radiofrequency (RF) current between the line segments;
    a bridge controller which controls the state of the electrically conductive bridge; and
    a measurement unit which measures the impedance across the line segments and the impedance bridge while the conductive bridge controlled to be in the open state.

2. The transmission line according to claim 1, wherein the impedance element includes at least one of a resistive, capacitive, or inductive element.

3. The transmission line according to claim 1, wherein the impedance element is a resistive wire.

4. The transmission line according to claim 1, wherein the impedance element is a conductive fluid with a corresponding resistance.

5. The transmission line according to claim 1, wherein the impedance (Z) of the impedance element is chosen to suppress common mode currents induced onto the transmission line segments when the electrically conductive bridge is in the open state.

6. The transmission line according to claim 1, further including:
  an active element disposed at an end of one of the line segments opposite the electrically conductive bridge; and
  an active element controller disposed at an end of the other line segment opposite the electrically conductive bridge.

7. The transmission line according to claim 1, wherein
  the electrically conductive bridge is a mechanically actuated switch; and
  the bridge controller provides mechanical force over a control line to actuate the mechanical switch.

8. The transmission line according to claim 1, wherein
  the electrically conductive bridge is a pressure actuated switch; and
  the bridge controller provides pneumatic and/or hydraulic force over a control line to actuate the pressure switch.

9. An interventional instrument comprising:
  an active element disposed adjacent a tip end;
  a transmission line according to claim 1, extending through the interventional instrument from the active element to a point of connection with associated electronic equipment.

10. A magnetic resonance system comprising:
  a magnet which generates a static magnetic field in an examination region;
  a radiofrequency coil configured to induce and manipulate magnetic resonance in a subject in the examination region and/or acquire magnetic resonance data from the examination region; and
  the interventional instrument including a transmission line according to claim 8.

11. The magnetic resonance system according to claim 10, further including:
  an active element connected with the transmission line and wherein the transmission line is electrically connected to an active element controller.

12. The magnetic resonance system according to claim 11, wherein the active element is sends data along the transmission line to the active element controller.

13. The magnetic resonance system according to claim 10, further including:
  a scanner controller which controls an RF transmitter connected to the radiofrequency coil based on the measured impedance of the measurement unit.

14. The magnetic resonance system according to claim 10, further including:
  a field sensor which detects a presence of an RF magnetic and/or electrical field; and
  wherein the bridge controller actuates the conductive bridges to an open state according to the field sensor.

15. The magnetic resonance system according to claim 10, further including:
  a temperature sensor which measure a temperature proximate the active element; and
  wherein the bridge controller actuates the conductive bridges to an open state according to the temperature sensor.

16. A method of using a transmission line which includes at least a pair of transmission line segments separated by a non-conductive gap, the non-conductive gap being bridged by a conductive bridge parallel to an impedance bridge, the method comprising:
  installing the transmission line in an interventional instrument, such as a catheter;
  controlling the conductive bridge to an open state such that the line segments are electrically decoupled; and
  measuring an impedance of the impedance bridge.

17. The method according to claim 16, further including:
  positioning a subject in a magnetic resonance imaging system;
  using the interventional instrument within the magnetic resonance imaging system;
  initiating magnetic resonance imaging while the interventional instrument is located in the magnetic resonance imaging system based on the measured impedance of the impedance bridge.

18. The method according to claim 16, further including:
  determining a difference between the measured impedance to a known impedance of the impedance bridge; and
  wherein the difference is below a predetermined threshold to initiate magnetic resonance imaging.

19. The method according to claim 18, wherein the transmission line includes a n pairs of transmission line segments along with corresponding n non-conductive gaps, conductive bridges, and impedance bridges and the impedance of each impedance bridge is Z, the method further including:
  initiating magnetic resonance imaging while the interventional instrument is located in the magnetic resonance imaging system if the measured impedance is substantially equal to nZ.

* * * * *